United States Patent

Poss

[11] Patent Number: 5,208,234
[45] Date of Patent: May 4, 1993

[54] SUBSTITUTED IMIDAZOLE PHOSPHONIC AND PHOSPHINIC ACID DERIVATIVES

[75] Inventor: Michael A. Poss, Lawrenceville, N.J.

[73] Assignee: E. R. Squibb & Sons, Inc., Princeton, N.J.

[21] Appl. No.: 851,373

[22] Filed: Mar. 10, 1992

[51] Int. Cl.[5] .............. A61K 31/535; A61K 31/415; C07D 413/14; C07F 9/28

[52] U.S. Cl. .................... 514/235.8; 514/255; 514/326; 514/396; 514/397; 514/398; 514/399; 514/400; 544/139; 544/337; 546/22; 548/111; 548/112

[58] Field of Search .................. 548/111, 112; 546/22; 544/139, 337; 514/235.8, 255, 326, 396, 397, 398, 399, 400

[56] References Cited

U.S. PATENT DOCUMENTS

| | | | |
|---|---|---|---|
| 4,340,598 | 7/1982 | Furukawa et al. | 424/273 R |
| 4,355,040 | 10/1982 | Furukawa et al. | 424/273 R |
| 4,582,847 | 4/1986 | Furukawa et al. | 514/400 |
| 4,820,843 | 4/1989 | Aldrich et al. | 548/252 |
| 4,870,186 | 9/1989 | Aldrich et al. | 548/215 |
| 4,874,867 | 10/1989 | Aldrich et al. | 548/101 |
| 4,880,804 | 11/1989 | Carini et al. | 514/234.5 |

FOREIGN PATENT DOCUMENTS

| | | | |
|---|---|---|---|
| 253310 | 1/1988 | European Pat. Off. | 514/400 |
| 323841 | 7/1989 | European Pat. Off. | 514/400 |
| 392317 | 10/1990 | European Pat. Off. | 548/325 |
| 400974 | 12/1990 | European Pat. Off. | 548/325 |
| 420237 | 4/1991 | European Pat. Off. | 548/325 |
| 429257 | 5/1991 | European Pat. Off. | 548/252 |

Primary Examiner—Mary C. Lee
Assistant Examiner—Joseph K. McKane
Attorney, Agent, or Firm—Ellen K. Park

[57] ABSTRACT

Novel compounds having the formula

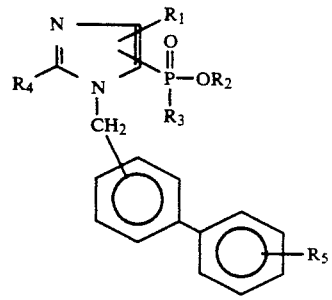

wherein $R_1$, $R_2$, $R_3$, $R_4$ and $R_5$ are as defined herein. These compounds inhibit the action of angiotensin II and are useful, therefore, for example, as antihypertensive agents.

8 Claims, No Drawings

SUBSTITUTED IMIDAZOLE PHOSPHONIC AND PHOSPHINIC ACID DERIVATIVES

FIELD OF THE INVENTION

The present invention relates to novel substituted imidazoles which are useful as antihypertensive agents.

SUMMARY OF THE INVENTION

In accordance with the present invention, novel compounds which inhibit the action of the hormone angiotensin II are disclosed. These compounds are of the general formula

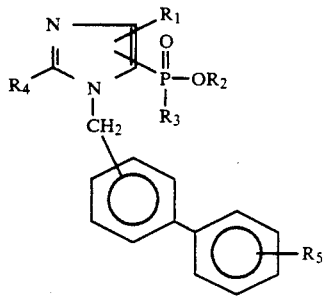

and pharmaceutically acceptable salts and prodrugs thereof.

As used in formula I, and throughout the specification, the symbols have the following meanings:

where $R_1$ is hydrogen, halogen, $-CF_3$ or $-CF_2CF_3$;
$R_2$ is hydrogen or $R_6$;
$R_3$ is hydroxy or $R_7$;
$R_4$ is alkyl, alkenyl or alkynyl or an alkyl, alkenyl or alkynyl group substituted with one or more F or $-CO_2R_8$ groups; cycloalkyl; (cycloalkyl)alkyl of 4 to 10 carbon atoms; (cycloalkyl)alkenyl or (cycloalkyl)alkynyl of 5 to 10 carbon atoms; $-NR_{11}R_{12}$; $-(CH_2)_nZ(CH_2)_pR_{14}$; benzyl or benzyl substituted with 1 or 2 halogens, alkoxy of 1 to 4 carbon atoms, alkyl of 1 to 4 carbon atoms, haloalkyl or nitro; $-SR_{15}$; or $-OR_{15}$;
$R_5$ is an acid moiety such as hydrogen,

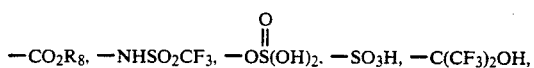

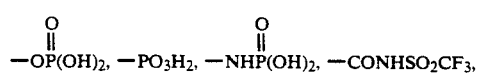

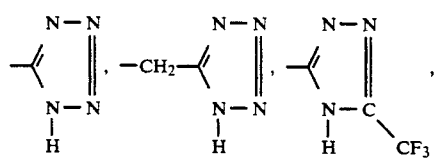

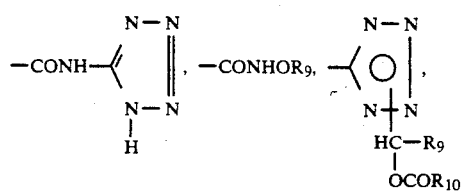

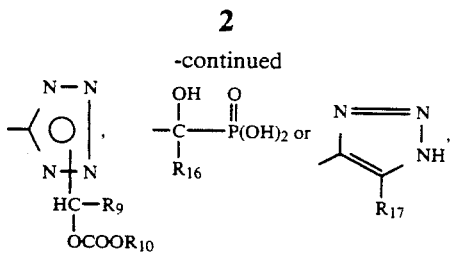

$R_6$ is alkyl of 1 to 6 carbon atoms, cycloalkyl of 3 to 6 carbon atoms, arylalkyl, alkylaryl or phenyl;
$R_7$ is alkyl of 1 to 6 carbon atoms, alkylaryl, cycloalkyl of 3 to 6 carbon atoms or $OR_6$;
$R_8$ is hydrogen, alkyl, perfluoroalkyl of 1 to 8 carbon atoms, cycloalkyl of 3 to 6 carbon atoms, phenyl, benzyl,

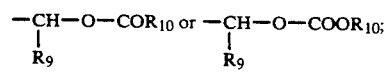

$R_9$ is hydrogen, alkyl, aryl, alkylaryl, arylalkyl or cycloalkyl;
$R_{10}$ is alkyl, aryl, alkylaryl, arylalkyl or cycloalkyl;
$R_{11}$ and $R_{12}$ are independently hydrogen, alkyl of 1 to 6 carbon atoms, benzyl, α-methylbenzyl, or taken together with the nitrogen atom to which they are attached form a ring of the formula

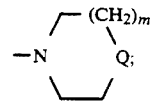

$R_{13}$ is hydrogen, alkyl of 1 to 6 carbon atoms, cycloalkyl of 3 to 6 carbon atoms, phenyl or benzyl;
$R_{14}$ is hydrogen; alkyl of 1 to 6 carbon atoms; cycloalkyl; alkenyl or alkynyl of 2 to 4 carbon atoms; or the above alkyl, cycloalkyl, alkenyl or alkynyl group optionally substituted with F or $-CO_2R_8$;
$R_{15}$ is alkyl, alkenyl, alkynyl, aryl, arylalkyl, cycloalkyl, (cycloalkyl)alkyl, heterocyclo, (heterocyclo)alkyl or haloalkyl;
$R_{16}$ is hydrogen, alkyl of 1 to 5 carbon atoms or phenyl:
$R_{17}$ is $-CN$, $-NO_2$ or $-CO_2R_8$;
Q is $-CH_2$, $-O-$, or $-NR_9$;
Z is $-O-$, $-S-$ or $-NR_{13}$;
m is 0, or the integer 1;
n is an integer of 1 to 5; and
p is an integer of 1 to 5.

DETAILED DESCRIPTION OF THE INVENTION

The present invention relates to the compounds of formula I (and pharmaceutically acceptable salts and prodrugs thereof), pharmaceutical compositions employing such compounds and to methods of using such compounds. Listed below are definitions of various terms used to describe the compounds of the instant invention. These definitions apply to the terms as they are used throughout the specification (unless they are otherwise limited in specific instances) either individually or as part of a larger group.

The term "alkyl" refers to both straight and branched chain groups having 1 to 10 carbon atoms. Alkyl groups having 1 to 4 carbon atoms are preferred.

The terms "alkenyl" and "alkynyl" refer to both straight and branched chain groups. Those groups having 2 to 10 carbon atoms are preferred.

The term "cycloalkyl" refers to groups having 3 to 8 carbon atoms.

The term "alkoxy" refers to groups having 1 to 8 carbon atoms. Alkoxy groups having 1 to 3 carbon atoms are preferred.

The term "halogen" refers to fluorine, chlorine, bromine and iodine with fluorine and chlorine being preferred.

The term "haloalkyl" refers to such alkyl groups described above in which one or more hydrogens have been replaced by chloro, bromo or fluoro groups such as trifluoromethyl, pentafluoroethyl, 2,2,2-trichloroethyl, chloromethyl, bromomethyl, etc., trifluoromethyl being preferred.

The term "aryl" refers to phenyl or naphthyl or phenyl or naphthyl substituted with substituents selected from halogen, alkyl, alkoxy, carboxy, alkylthio, hydroxy, alkanoyl, nitro, amino, alkylamino, dialkylamino or trifluoromethyl groups. Preferred aryl groups are phenyl and monosubstituted phenyl and phenyl is most preferred.

The term "heterocyclo" refers to fully saturated or unsaturated rings of 5 or 6 atoms containing one to four nitrogen atoms, or one oxygen atom, or one sulfur atom, or one oxygen atom and one or two nitrogen atoms, or one sulfur atom and one or two nitrogen atoms. Preferred monocyclic heterocyclo groups include 2- and 3-thienyl, 2- and 3-furyl, 2-, 3- and 4-pyridyl, and imidazolyl. The heterocycle may also have a substituent selected from alkyl of 1 to 4 carbons, carboxy, alkoxy of 1 to 4 carbons and alkylthio of 1 to 4 carbons on an available carbon. The term heterocyclo also includes bicyclic rings wherein the five or six membered ring containing oxygen, sulfur and nitrogen atoms as defined above is fused to a benzene ring. It is preferred that the bicyclic ring is attached by way of an available carbon atom in the benzene ring. Examples of such preferred bicyclic heterocyclo groups include 4, 5, 6 or 7-indolyl, 4, 5, 6 or 7-isoindolyl, 5, 6, 7 or 8-quinolinyl, 5, 6, 7 or 8-isoquinolinyl, 4, 5, 6, or 7-benzothiazolyl, 4, 5, 6 or 7-benzoxazolyl, 4, 5, 6 or 7-benzimidazolyl, 4, 5, 6 or 7-benzoxadiazolyl, and 4, 5, 6 or 7-benzofuranyl. Preferred fused heterocycles include thienyl, furyl, pyridyl and imidazolyl, optionally substituted as described above.

All stereoisomers of the compounds of the instant invention are contemplated, either in admixture or in pure or substantially pure form.

It should be understood that the present invention includes prodrug forms, such as ester, acetal and/or mixed acetal derivatives of the compounds of formula I. For example, such derivatives have been documented in *Design of Prodrugs*, edited by H. Bundgard, (Elsevier. 19B5) and *Methods in Enzymology*, Vol. 42, p. 309–396, edited by K. Widder et al. (Academic Press, 1985). Further, it is understood that any moiety at $R_2$, $R_3$ or $R_5$ that will be cleaved in vivo to provide an acidic $R_2$, $R_3$ or $R_5$ moiety is within the spirit and scope of this invention.

An exemplary process for preparing the compounds of formula I where $R_2$ is $R_6$ and $R_3$ is $R_7$, includes coupling a compound of the formula

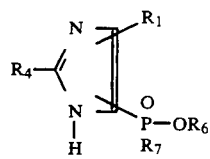
II with a compound of the formula

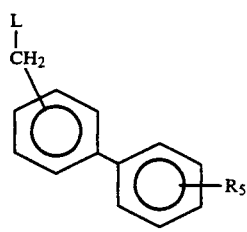
III wherein L is a leaving group such as a halogen, in the presence of a coupling agent such as cesium carbonate, in an organic solvent such as tetrahydrofuran or dimethylformamide to form compounds of formula

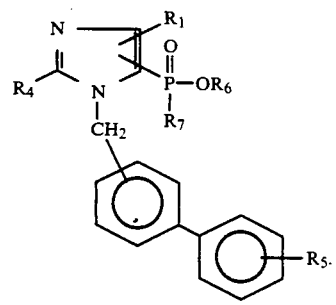
Ia

De-esterification of the formula Ia compounds by subsequent treatment with a base such as potassium hydroxide or a Lewis acid such as trimethylsilylbromide provides the other compounds of formula I (i.e. where $R_2$ is hydrogen and $R_3$ is hydroxy).

The imidazole II can be prepared by reacting imidazole with an orthoester such as triethyl ortho formate in the presence of an acid such as para-toluenesulfonic acid to form a compound of formula

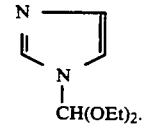
V

Compounds of formula V are then reacted with a strong base such as n-butyllithium in an organic solvent such as tetrahydrofuran and alkylated with an alkyl halide such as n-butyliodide (R<=n-butyl) to form compounds of formula

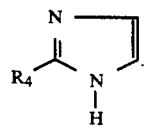
VI

Compounds of formula VI are then halogenated with bromine (hal=Br) or NCS (hal=Cl) in an organic solvent such as chloroform to form compounds of formula

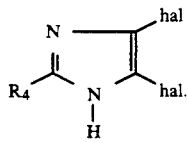
VII

Compounds of formula VII are then reacted with a protecting group such as 2-(trimethylsilyl)-ethoxymethyl chloride and a base such as sodium hydride in an organic solvent such as tetrahydrofuran to form compounds of formula

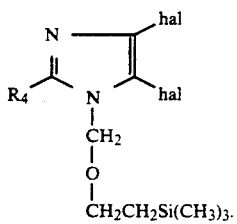
VIII

Compounds of formula VIII may then be reacted with a strong base such as n-butyllithium followed by a compound of formula hal-PO(OR$_6$)R$_7$ such as diethylchlorophosphate in an organic solvent such as tetrahydrofuran to form

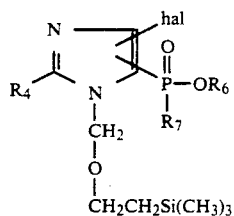
IX where R$_7$ is OR$_6$. To form compounds of formula IX where R$_7$ is other than OR$_6$, compounds of formula VIII are reacted with a compound of formula ClP(OR$_6$)$_2$ to form compounds of formula

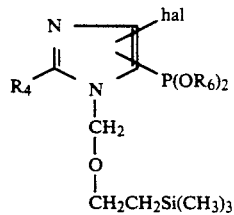
X which is then treated with, for example, an alkyl halide such as methyl iodide (R$_7$=methyl) to form the compounds of formula IX where R$_7$ is other than OR$_6$.

Treatment of formula IX compounds with an acid such as hydrochloric acid in an organic solvent such as tetrahydrofuran, to remove the protecting group provides the formula II compounds where R$_1$ is halogen. To obtain compounds of formula II where R$_1$ is hydrogen, compounds of formula IX are first reacted with hydrogen, in the presence of a catalyst such as Pd/(OH)$_2$, in an organic solvent such as ethanol prior to deprotection with the acid. Compounds of formula II where R$_1$ is —CF$_3$ or —CF$_2$CF$_3$ may be prepared by methods similar to those described above using, for example, 4-trifluoromethyl imidazole (J. J. Baldwin et al., *J. Med. Chem.*, 18, 895, 1975).

Compounds of formula III can be prepared by methods disclosed in European Patent Application No. 0253310, to E. I. DuPont de Nemours and Co., published Jan. 20, 1988 and U.S. Pat. No. 4,870,186, issued Sept. 26, 1986 to Aldrich et al.

Preferred compounds of the present invention are those wherein

R$_1$ is hydrogen or halogen;
R$_2$ is hydrogen or an alkyl of 1 to 6 carbon atoms;
R$_3$ is alkyl of 1 to 6 carbon atoms, —OH or —O—alkyl of 1 to 6 carbon atoms;
R$_4$ is an alkyl of 2 to 10 carbon atoms or alkenyl of 3 to 10 carbon atoms; and
R$_5$ is ortho-tetrazolyl or —CO$_2$H.

Most preferred are compounds of formula I wherein

R$_1$ is bromine or chlorine;
R$_2$ is ethyl;
R$_3$ is —OH;
R$_4$ is n-butyl; the imidazole nucleus is bonded to the para-position of the biphenyl portion; and
R$_5$ is ortho-tetrazolyl.

The present compounds of formula I inhibit the action of the hormone angiotensin II (A-II) and are therefore useful, for example, as antihypertensive agents.

The action of the enzyme renin on angiotensinogen, a pseudoglobulin in blood plasma, produces angiotensin I. Angiotensin I is converted by angiotensin converting enzyme (ACE) to A-II. The latter is an active pressor substance which has been implicated as the causative agent in several forms of hypertension in various mammalian species, e.g., humans. The compounds of this invention inhibit the action of A-II at its receptors on target cells and thus prevent the increase in blood pressure produced by this hormone-receptor interaction. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg per kilogram of body weight per day, preferably about 1 to 15 mg per kilogram of body weight per day is appropriate to reduce blood pressure. The substance is preferably administered orally, but intranasal, transdermal and parenteral routes such as the subcutaneous, intramuscular, intravenous or intraperitoneal routes can also be employed. The compounds of this invention are also useful in the treatment of congestive heart failure and cardiac hypertrophy. In addition, in view of the role of these compounds in the renin-angiotensin system described above, the A-II antagonist compounds disclosed herein are also expected to be useful for the same or similar indications which have developed for ACE inhibitors.

The compounds of this invention can also be formulated in combination with a diuretic for the treatment of hypertension. A combination product comprising a compound of this invention and a diuretic can be administered in an effective amount which comprises a total daily dosage of about 30 to 600 mg, preferably about 30 to 330 mg of a compound of this invention, and about 15 to 300 mg, preferably about 15 to 200 mg of the diuretic, to a mammalian species in need thereof. Exemplary of the diuretics contemplated for use in combination with a compound of this invention are the thiazide diuretics, e.g., chlorthiazide, hydrochlorthiazide, flumethiazide, hydroflumethiazide, bendroflumethiazide, methylchlothiazide, trichlormethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, in sterile solutions or suspensions for parenteral or intranasal administration, or in transdermal patches. About 10 to 500 mg of a compound of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples and preparations describe the manner and process of making and using the invention and are illustrative rather than limiting. It should be understood that there may be other embodiments which fall within the spirit and scope of the invention as defined by the claims appended hereto.

EXAMPLE

[4-Bromo-2-butyl-1-[[2'-(2H-tetrazol-5-yl)[1,1'biphenyl]-4-yl]methyl]-1H-imidazol-5-yl]phosphonic acid, ethyl ester, dipotassium salt

A. (4-Bromo-2-butyl-1H-imidazol-5-yl)phosphonic acid, diethyl ester

1. 1-(Diethoxymethyl)-1H-imidazole

A mixture of imidazole (15 g, 0.220 mol, 1 eq), triethyl orthoformate (130 g, 146.6 mL, 0.880 mol, 4, eq) and p-toluenesulfonic acid (1.17 g, 0.00616 mol, 0.028 eq) was heated at 145°-175° C. until no more ethanol was distillable from the reaction mixture. The excess orthoformate was removed in vacuo. Solid sodium bicarbonate (1.17 g, 0.011 mol) was added and the residue was vacuum distilled to give the title compound (23.6 g, 68%). b.p. 89°-91° C./0.3 mm Hg.

2. 2-Butyl-1H-imidazole

To the title 1 compound (22.350 g, 142.181 mmol, 1 eq) in dry tetrahydrofuran (355 mL, 0.4 M) at −40° C. was added via syringe n-butyllithium (2.5 M in hexane, 56.87 mL, 142.181 mmol, 1 eq) such that the temperature did not rise above −35° C. The mixture was stirred at −40° C. for 15 minutes. n-Butyl iodide (31.397 g, 170.617 mmol, 1.2 eq) was added over 5 minutes at −40° C., and the mixture was warmed to room temperature overnight. Ether (350 mL) was then added. The mixture was extracted with 0.1 N hydrochloric acid (4×350 mL). The acid extracts were neutralized with solid sodium bicarbonate and extracted with methylene chloride (6×700 mL). The organic extracts were dried (magnesium sulfate) and concentrated to give the title compound (14.7 g, 83%).

3. 2-Butyl-1-[[2-(trimethylsilyl)ethoxy]methyl]-1H-imidazole

To the title 2 compound (4.160 g, 33.498 mmol, 1 eq) in tetrahydrofuran (83.7 mL, 0.4 M) at 0° C., sodium hydride (1.125 g, 46.897 mmol, 1.4 eq) was added. The mixture was stirred at 0° C. for 30 minutes and at room temperature for 15 minutes. The reaction was cooled to 0° C. and 2-(trimethylsilyl)ethoxymethyl chloride (7.114 mL, 40.197 mmol, 1.2 eq) was added. The mixture was warmed to room temperature and stirred for 0.5 hours. Saturated ammonium chloride was added and the liquid was extracted with ethyl acetate. The extracts were dried (magnesium sulfate) and concentrated. The residue was chromatographed on silica gel eluting with hexane:ethyl acetate:triethylamine (100:50:0.2) to give the title compound (5.430 g, 64%).

4. 4,5-Dibromo-2-butyl-1-[[2-(trimethylsilyl)ethoxy]methyl]-1H-imidazole

To the title 3 compound (6.466 g, 25.412 mmol, 1 eq) in chloroform (50.8 mL, 0.5 M) at 0° C., bromine (2.669 mL, 52.094 mmol, 2.05 eq) in chloroform (50.8 mL, 1.04 M) was added dropwise. The reaction was warmed to room temperature and stirred for two hours. The reaction mixture was neutralized with cool potassium carbonate water solution and extracted with methylene chloride. The extracts were dried (magnesium sulfate) and concentrated. The residue was chromatographed on silica gel eluting with hexane:ethyl acetate: triethylamine (100:5:0.15) to give the title compound (7.15 g, 68%).

5. [4-Bromo-2-butyl-1-[[2-(trimethylsilyl)ethoxy]methyl]-1H-imidazol-5-yl]phosphonic acid, diethyl ester To the title 4 compound (3.246 g, 7.874 mmol, 1 eq) in tetrahydrofuran (31.5 mL, 0.25 M) at −78° C., n-butyl lithium (2.39 M in hexane, 3.62 mL, 8.661 mmol, 1.1 eq) was added. The mixture was stirred at −78° C. for 5 minutes. Diethyl chlorophosphate (1.365 mL, 9.45 mmol, 1.2 eq) was added. The reaction was stirred at −78° C. for 10 minutes and at room temperature for 1 hour. Saturated ammonium chloride water solution was added. The mixture was extracted with methylene chloride. The extracts were washed with brine, dried (magnesium sulfate) and concentrated. The residue was chromatographed on silica gel eluting with chloroform:ethyl acetate:triethylamine (80:10:0.2) to give the title compound (2.266 g, 61%).

6. (4-Bromo-2-butyl-1H-imidazol-5-yl)-phosphonic acid, diethyl ester

A mixture of the title 5 compound (1.020 g, 2.173 mmol), ethanol (20 mL) and 3 N hydrochloric acid (20 mL) was heated at 50° C. for 2 hours and 15 minutes. The reaction mixture was neutralized with solid sodium bicarbonate and sodium bicarbonate water solution and then was extracted with ethyl acetate. The extracts were dried (magnesium sulfate) and concentrated to give the title compound (703 mg, 95%).

B. 5-(4'-(Bromomethyl)[1 1'-biphenyl]-2yl]-1-(triphenylmethyl)-2H-tetrazole

4'-Methyl[1,1'-biphenyl]-2-carboxamide

To a solution of 4'-Methyl[1,1'-biphenyl]-2-carboxylic acid, prepared as in European Patent Application 87-109919.8 Example 85-a, page 147, line 32 (20.0 g, 94.2 mmol) in dichloromethane (200 mL) at 0° C. was added dimethylformamide (0.5 mL) followed by oxalyl chloride (375 mL of 2.0 M solution in dichloromethane, 750 mmol). The rate of addition was adjusted to maintain the internal temperature below 10° C. When the addition was complete, the mixture was allowed to warm to 25° C. and was stirred at that temperature for two hours, after which it was concentrated in vacuo. The semisolid residue was added portionwise to concentrated ammonium hydroxide solution (250 mL) at 0° C., stirred for 15 minutes, and diluted with water (200 mL). The resulting white precipitate was collected, washed with water, and dried in vacuo over phosphorus pentoxide to give the title compound (18.7 g, 90%).

2. 4'-Methyl[1,1'-biphenyl]-2-carbonitrile

A mixture of the title 1 compound (18.7 g, 88.4 mmol) and thionyl chloride (90 mL) was heated at reflux for four hours, after which it was concentrated in vacuo. The resulting brown solid was crystallized from hexanes (500 mL) to give the title compound in two crops (13.5 g, 80%); m.p. 44°-47° C.

3. 5-(4'-Methyl[1,1'-biphenyl]-2-yl)-1-(triphenylmethyl)-2H-tetrazole (Prepared by a modification of Example 17 in European patent application EP 0324377).

A mixture of the title 2 compound (9 g, 46.6 mmol), trimethyltin chloride (10.2 g, 51.2 mmol), and sodium azide (3.03 g, 46.6 mmol) in toluene (35 mL) was heated for 31 hours in a 110° C. oil bath. The reaction mixture was cooled, additional toluene (15 mL) was added and the reaction heated at 110° C. for 48 hours, cooled, and diluted with more toluene (35 mL). Triphenylmethyl chloride (13.5 g, 48.4 mmol) and 10N aqueous sodium hydroxide (5.5 mL) were added and the stoppered reaction was stirred at room temperature overnight. The reaction mixture was next treated with water (35 mL) and heptane (70 mL) and rapidly stirred for two hours while cooled in an ice-water bath. The precipitated solid was collected by filtration using two rinses of water (50 mL) and a rinse of heptane:toluene (50 mL; 3:2, vol:vol). Further solid product precipitated from the filtrate, and the weight of the combined solid (undried) was 19.6 grams. This crude product was partitioned between methylene chloride (200 mL) and sodium hydroxide (0.5N, 50 mL). The organic layer was rinsed with brine (50 mL), dried (sodium sulfate), filtered over Celite, and concentrated in vacuo. Trituration of the resulting solid yielded the title compound (14.1 g, 63% yield); m.p. s144, 154°-159° C.(d).

4. 5-(4'-(Bromomethyl)[1,1'-biphenyl]-2-yl]-1-(triphenylmethyl)-2H-tetrazole (Prepared following the procedure for Example 6 in U.S. Pat. No. 4,870,186).

A solution containing the title 3 compound (310 mg, 0.648 mmol), N-bromosuccinimide (115 mg, 0.646 mmol), and benzoyl peroxide (11 mg, 0.045 mmol) in carbon tetrachloride (4 mL) was refluxed for three hours, then cooled to 40° C. and filtered. Evaporation of the filtrate followed by trituration using isopropyl ether gave the title compound (275 mg, 76% yield) contaminated by di-brominated compound (15% by hplc and H-nmr analysis); m.p. 127°-134° C.

C. [4-Bromo-2-butyl-1-[[2'-[2-(triphenylmethyl)-2H-tetrazol-5-yl][1,1'-biphenyl]-4-yl]-methyl]-1H-imidazol-5-yl]phosphonic acid, diethyl ester The title A compound (30.7 mg, 0.09051 mmol, 1.0 eq), the title B compound (55.5 mg, 0.09957 mmol, 1.1 eq), and cesium carbonate (36.9 mg, 0.1131 mmol, 1.25 eq), in dimethylformamide (0.36 mL, 0.25M) were combined and stirred at 0° C. overnight. The mixture was then diluted with ethyl acetate and filtered. The filtrate was combined with pH 4 buffer and extracted three times with ethyl acetate. The organic extracts were dried over sodium sulfate, filtered through magnesium sulfate, and concentrated. The residue was chromatographed on Merck silica gel (5 g) eluting with toluene::ethyl acetate:triethyl amine (25:5:0.05) to give the title compound (46.6 mg, 63%).

D. [4-Bromo-2-butyl-1-[[2'-[2H-tetrazol-5-yl]-[1,1'-biphenyl]-4-yl]methyl]-1H-imidazol-5-yl]phosphonic acid, diethyl ester The title C compound (435.6 mg), tetrahydrofuran (5 mL) ethanol (5 mL), and 10% hydrochloric acid (5 mL) were combined and stirred at room temperature for three hours. The solution was then concentrated and the residue was chromatographed on Merck silica gel (20 g) eluting with chloroform: methanol:acetic acid (30:0.7:0.05) followed by (30:1:0.05) to give the title compound (190.0 mg, 62%).

E. [4-Bromo-2-butyl-1-[[2'-(2H-tetrazol-5-yl)-[1,1'-biphenyl]-4-yl]methyl]-1H-imidazol-5-yl]phosphonic acid, ethyl ester, dipotassium salt The title D compound (190.0 mg, 0.3313 mmol, 1.0 eq) was combined with 1N potassium hydroxide (1.0 mL, 0.9940 mmol, 3.0 eq) in ethanol (1.0 mL) at 50° C. for a total of 2.5 days. The mixture was concentrated and then chromatographed on an HP-20 column (10 g) eluting with water (70 mL), 3% acetone (60 mL), 6% acetone (60 mL), 12% acetone (60 mL) and 20% acetone (60 mL). The product fractions were concentrated, then dissolved in water (20 mL, filtered and lyophilized to furnish the title compound (201.3 mg, 98%); m.p. >240° C.

| Element Analysis (%) | |
| --- | --- |
| Calc'd: | C 42.71; H 4.18; N 12.99; Br 12.35; P 4.79; |
| Found: | C 42.76; H 4.45; N 12.80; Br 12.25; P 4.67. |

What is claimed is:

1. A compound of the formula

[Structure I: imidazole ring with N=C(R4)-N-CH2-biphenyl-R5, with R1 at position and P(=O)(OR2)(R3) group]

or a pharmaceutically acceptable salt or prodrug thereof where $R_1$ is hydrogen, halogen, —$CF_3$ or —$CF_2CF_3$;

$R_2$ is hydrogen or $R_6$;

$R_3$ is hydroxy or $R_7$;

$R_4$ is alkyl, alkenyl or alkynyl or an alkyl, alkenyl or alkynyl group substituted with one or more F or —$CO_2R_8$ groups; cycloalkyl; (cycloalkyl)alkyl of 4 to 10 carbon atoms; (cycloalkyl)alkenyl or (cycloalkyl)alkynyl of 5 to 10 carbon atoms; —$NR_{11}R_{12}$; —$(CH_2)_nZ(CH_2)_pR_{14}$; benzyl or benzyl substituted with 1 or 2 halogens, alkoxy of 1 to 4 carbon atoms, alkyl of 1 to 4 carbon atoms, haloalkyl or nitro; —$SR_{15}$; or —$OR_{15}$;

$R_5$ is an acid moiety such as hydrogen,

—$CO_2R_8$, —$NHSO_2CF_3$, —$OS(OH)_2$, —$SO_3H$, —$C(CF_3)_2OH$, $$\overset{O}{\underset{\|}{}}$$

—$OP(OH)_2$, —$PO_3H_2$, —$NHP(OH)_2$, —$CONHSO_2CF_3$,

[various tetrazole and heterocyclic substituent structures]

$R_6$ is alkyl of 1 to 6 carbon atoms, cycloalkyl of 3 to 6 carbon atoms, arylalkyl, alkylaryl or phenyl;

$R_7$ is alkyl of 1 to 6 carbon atoms, alkylaryl, cycloalkyl of 3 to 6 carbon atoms or $OR_6$;

$R_8$ is hydrogen, alkyl, perfluoroalkyl of 1 to 8 carbon atoms, cycloalkyl of 3 to 6 carbon atoms, phenyl, benzyl, —CH(R_9)—O—COR_{10} or —CH(R_9)—O—COOR_{10};

$R_9$ is hydrogen, alkyl, aryl, alkylaryl, arylalkyl or cycloalkyl;

$R_{10}$ is alkyl, aryl, alkylaryl, arylalkyl or cycloalkyl;

$R_{11}$ and $R_{12}$ are independently hydrogen, alkyl of 1 to 6 carbon atoms, benzyl, α-methylbenzyl, or taken together with the nitrogen atom to which they are attached form a ring of the formula

[ring structure with —N, (CH2)m, Q]

$R_{13}$ is hydrogen, alkyl of 1 to 6 carbon atoms, cycloalkyl of 3 to 6 carbon atoms, phenyl or benzyl;

$R_{14}$ is hydrogen; alkyl of 1 to 6 carbon atoms; cycloalkyl; alkenyl or alkynyl of 2 to 4 carbon atoms; or the above alkyl, cycloalkyl, alkenyl or alkynyl group optionally substituted with F or —$CO_2R_8$;

$R_{15}$ is alkyl, alkenyl, alkynyl, aryl, arylalkyl, cycloalkyl, (cycloalkyl)alkyl, heterocyclo, (heterocyclo)alkyl or haloalkyl;

$R_{16}$ is hydrogen, alkyl of 1 to 5 carbon atoms or phenyl;

$R_{17}$ is —CN, —$NO_2$ or —$CO_2R_8$;

Q is —$CH_2$, —O—, or —$NR_9$;

Z is —O—, —S— or —$NR_{13}$;

m is 0, or the integer 1;

n is an integer of 1 to 5; and p is an integer of 1 to 5.

2. A compound of claim 1 wherein
$R_1$ is hydrogen or halogen;
$R_2$ is hydrogen or an alkyl of 1 to 6 carbon atoms;
$R_3$ is alkyl of 1 to 6 carbon atoms, —OH or —O—alkyl of 1 to 6 carbon atoms;
$R_4$ is an alkyl of 2 to 10 carbon atoms or alkenyl of 3 to 10 carbon atoms; and
$R_5$ is ortho-tetrazolyl or —$CO_2H$.

3. A compound of claim 1 wherein
$R_1$ is bromine chlorine;
$R_2$ is ethyl;
$R_3$ is —OH;
$R_4$ is n-butyl; the imidazole nucleus is bonded to the para-position of the biphenyl portion; and
$R_5$ is ortho-tetrazolyl.

4. A compound of claim 1, [4-Bromo-2-butyl-1-[[2'-(2H-tetrazol-5-yl)[1,1'-biphenyl]-4-yl]methyl]-1H-imidazol-5-yl]phosphonic acid, ethyl ester, or a pharmaceutically acceptable salt or prodrug thereof.

5. A pharmaceutical composition comprising a compound of claim 1 and a pharmaceutically acceptable carrier.

6. A method for treating hypertension comprising administering to a mammalian specie in need thereof a therapeutically effective amount of a composition of claim 5.

7. A method for treating congestive heart failure comprising administering to a mammalian specie in need thereof a therapeutically effective amount of a composition of claim 5.

8. A method for preventing cardiac hypertrophy comprising administering to a mammalian specie in need thereof a therapeutically effective amount of a composition of claim 5.

* * * * *